United States Patent [19]

Cooper et al.

[11] Patent Number: 4,757,044
[45] Date of Patent: Jul. 12, 1988

[54] LANTHANIDE METAL SALTS OF HETEROPOLYANIONS AS CATALYSTS FOR ALCOHOL CONVERSION

[75] Inventors: Arthur J. Cooper, Garfield Heights; Frederick A. Pesa, Aurora; Janie K. Currie, Russell, all of Ohio

[73] Assignee: The Standard Oil Company, Cleveland, Ohio

[21] Appl. No.: 724,236

[22] Filed: Apr. 17, 1985

[51] Int. Cl.$^4$ .............................................. C08K 3/22
[52] U.S. Cl. ................................. 502/204; 502/206; 502/209; 502/210; 502/211; 502/302; 502/308; 502/311; 502/312; 502/321
[58] Field of Search ............... 502/204, 206, 209, 302, 502/308, 311, 312, 321, 210, 211

[56] References Cited

U.S. PATENT DOCUMENTS

| | | | |
|---|---|---|---|
| 4,172,051 | 10/1979 | Matsumoto et al. | 502/210 |
| 4,184,981 | 1/1980 | Vanderspurt | 502/210 |
| 4,192,251 | 3/1980 | Slinkard et al. | 562/549 |
| 4,192,776 | 3/1980 | Grasselli et al. | 502/210 |
| 4,271,040 | 6/1981 | Khoobiar | 502/210 |
| 4,359,407 | 11/1982 | Dolhyj et al. | 502/302 |
| 4,418,007 | 11/1983 | Derrien | 502/312 |
| 4,419,270 | 12/1983 | Ueshima et al. | 502/209 |
| 4,438,217 | 3/1984 | Takata et al. | 502/311 |
| 4,440,948 | 4/1984 | Oda et al. | 502/209 |
| 4,444,906 | 4/1984 | Callahan et al. | 502/210 |

FOREIGN PATENT DOCUMENTS

| | | |
|---|---|---|
| 0014908 | 7/1977 | Japan . |
| 0122734 | 3/1979 | Japan . |
| 0163755 | 5/1980 | Japan . |
| 0099426 | 8/1981 | Japan . |
| 0131527 | 10/1981 | Japan . |
| 0046925 | 3/1982 | Japan . |
| 2097382 | 4/1981 | United Kingdom . |

OTHER PUBLICATIONS

MacZura et al., "Alumina Compounds", reprint from *Kirk-Othmer Encyclopedia of Chemical Technology*, v. 2 3rd ed., pp. 225–234, (1978).
Hayashi et al., "Methanol Conversion over Metal Salts of 12-Tungstophosphoric Acid", *J. Catalysis*, 81, pp. 61–66, (1983).
Hayashi et al., "The Properties of Heteropoly Acids and the Conversion of Methanol to Hydrocarbons", *J. Catalysis*, 77, pp. 473–484, (1982).
Misono et al., "The Structure and Properties of 12-Heteropoly Acids of Molybdenum and Tungsten and Their Salts Pertinent to Heterogeneous Catalysis", Bul. Chem. Soc. Japan 55, pp. 400–406, (1982).
Ono et al., "Conversion of Methanol into Hydrocarbons over Silver Dodecatungstophosphate", presented at the Pan-Pacific Synfuels Conf., 1982.
Williams et al., "Organic Pigments", *Ind. Engr. Chem.*, Aug. 1955, v. 47, No. 8, pp. 1507–1510.
Clark, "Basic Dye–Heteropoly Acid Complexes for Printing Anionic Synthetic Fibers", Chem. Abst. 3705s.
Tomioka et al., "Cerium Catalyzed Selective Oxidation of Secondary Alcohols in the Presence of Primary Ones", *Tetrahedron Letters*, v. 23, No. 5, pp. 539–542, (1982).
Klinkenberg et al., "Polymerization of Ethylene on Heteropoly Acids as Catalysts", *Ref. Zh. Khim.*, 1962, Abst. 9L6.
Ono et al., "Conv. of Methanol into Hydrocarbons Catalysed by Metal Salts of Heteropolyacids", *JCS Chem. Comm.*, 1981, pp. 400–401.
Baba et al., "The Conversion of Methanol into Hydrocarbons over Dopecatoungstophosphoric Acid", Bull. Chem. Soc. Jan., v. 55, pp. 2555–2559, (1982).

*Primary Examiner*—John Doll
*Assistant Examiner*—Jeffrey Edwin Russel
*Attorney, Agent, or Firm*—M. F. Esposito; D. J. Untener; L. W. Evans

[57] ABSTRACT

A new catalyst system for the conversion of short-chain aliphatic alcohols to hydrocarbon having the formula

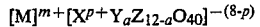

$$[M]^{m+}[X^{p+}Y_aZ_{12-a}O_{40}]^{-(8-p)}$$

wherein M is selected from at least one element from Group IIIA including lanthanides and actinides, or mixtures thereof,
X is at least one element selected from P, Si, As, Ti, Zr, B, Co, Cu or Sn,
Y and Z are independently selected from W, Mo, or V,
P=is the valence of X usually within 2 to 5,
m=8-p
$0 < a \leq 12$.

4 Claims, No Drawings

LANTHANIDE METAL SALTS OF HETEROPOLYANIONS AS CATALYSTS FOR ALCOHOL CONVERSION

BACKGROUND OF THE INVENTION

The present invention relates to a new catalyst system and a process for using this catalyst for the conversion of short chained alcohols such as methanol to hydrocarbons. In particular, the present invention is directed to a new catalyst system used in a process of the conversion of methanol to lower unsaturated hydrocarbons in the $C_2$-$C_4$ range.

The catalytic conversion of methanol to hydrocarbons is a well-known process. Many different catalysts have been described in the literature as effective in this process. For example, it has been demonstrated that zeolite-based catalysts, metal sulfates, metal phosphates, and heteropolyacids can be used as catalysts for the conversion of methanol to hydrocarbons.

Recently, industrial commitment to methanol conversion or upgrading has increased for a number of reasons, one of which is its availability from several different feedstocks. Moreover, heteropolyacid catalysts for use in methanol conversion have been attracting attention since they show activity even at temperatures as low as 300° C. because of their strong acidity. In Japanese Patent Application No. 121,018, heteropolyacids are disclosed as being suitable for the conversion of short chained alcohols or oxygen containing compounds to hydrocarbons. The conditions for the reaction are from a temperature range of 250°-400° C. at a pressure of between ambient to 200 kg/cm$^2$g, and in the LHSV range of 0.1-10 hours$^{-1}$.

The heteropolyacid described in this Japanese patent application includes many compounds which vary depending on the condensed coordination elements, the central elements and the condensation forms. The Japanese patent application specifically discloses that the hydrogen ions of the heteropolyacids are easily exchanged with other cations such as alkali metals including lithium, sodium, potassium, etc., nickel, cobalt, copper, manganese, lanthanide, silver, cesium, etc., to form the stable heteropolyacid salt. Moreover, the Japanese patent application discloses that these materials when applied to supports such as clay or zeolite, give improved conversion in the manufacture of the hydrocarbons.

Unfortunately, even the results achieved by the use of supported heteropolyacids/salts leave much to be desired. Accordingly, there is still significant room for improvement in the use of heteropolyacids/salts for the conversion of methanol to short-chained hydrocarbons. The present invention is directed to an improvement in the catalyst system used and the process for conversion of methanol to the short-chained hydrocarbons, and in particular, unsaturated short-chained hydrocarbons such as ethylene, propylene and butylene.

SUMMARY OF THE INVENTION

It is the primary object of the present invention to provide a new catalyst system for use in conversion of short-chained aliphatic alcohols to hydrocarbons.

It is another object of the present invention to provide a supported catalyst system for use in conversion of short chained aliphatic alcohols to hydrocarbons.

It is a further object of the present invention to provide a new catalyst for a process for the conversion of methanol to hydrocarbons.

It is still another object of the present invention to provide a process for the conversion of methanol to short-chained hydrocarbons by using a heteropolyacid salt catalyst.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the novel catalyst system of the present invention comprises a heteropolyacid salt having the following formula:

$$[M]^{m+}[X^{p+}Y_aZ_{12-a}O_{40}]^{-(8-p)}$$

wherein:

M is at least one element selected from Group IIIA, including the lanthanides and actinides, or mixtures thereof, X is at least one element selected from P, Si, As, Ti, Zr, B, Co, Cu or Sn, Y and Z are independently selected from W, Mo, or V, p = is the valence of X, usually within 2 to 5, m = 8 − p 0 < a ≦ 12.

In another aspect of the present invention, the catalyst system comprises a supported heteropolyacid salt catalyst having the formula:

$$[M]^{m+}[X^{p+}Y_aZ_{12-a}O_{40}]^{-(8-p)}$$

wherein:

M is at least one element selected from Group IIIA, including the lanthanides and actinides, or mixtures thereof, X is at least one element selected from P, Si, As, Ti, Zr, B, Co, Cu or Sn, Y and Z are independently selected from W, Mo, or V, p = is the valence of X, usually within 2 to 5, m = 8 − p 0 < a ≦ 12 and said support has a surface area in the range of greater than about 10 m$^2$/gm.

In a further aspect of the present invention, a process for the conversion of aliphatic oxygen containing organic compounds to hydrocarbons comprises placing a catalyst having the formula:

$$[M]^{m+}[X^{p+}Y_aZ_{12-a}O_{40}]^{-(8-p)}$$

wherein M, X, Y and Z are defined as described above, m = 8 − p, and 0 < a ≦ 12 in a reactor, passing an aliphatic oxygen containing organic compound over said catalyst at an elevated temperature for a time sufficient to convert the alcohol to the corresponding hydrocarbons, and recovering the hydrocarbons.

In a preferred embodiment of the process of the present invention, the catalyst is supported on a material having a surface area greater than about 10 m$^2$/gm, most preferably a surface area greater than 50 m²/gm. The support material may be inert.

The catalyst of the present invention offers significant advantages over the catalyst described in the previous procedures. The catalyst of the present invention exhibits superior selectivity to olefin production over other transition metal salts. Moreover, the present invention offers greater ease of preparation than the zeolites used in the procedures described previously. The heteropolyacids are rapidly precipitated from solutions by the lanthanide or actinide cations thereby avoiding prolonged hydrothermal crystallization which is characteristic of zeolite catalyst manufacture.

DETAILED DESCRIPTION OF THE INVENTION

Catalysts

The catalyst of the present invention are lanthanide or actinide salts of heteropolyacids. The catalyst can be used in the conversion of methanol to $C_1$ to $C_7$ hydrocarbons, in particular short chained unsaturated olefins such as ethylene and propylene.

The heteropolyacid salt catalyst of the present invention has the formula:

$$[M]^{m+}[X^{p+}Y_aZ_{12-a}O_{40}]^{-(8-p)}$$

wherein:
M is at least one element selected from Group IIIA, including the lanthanides and actinides, or mixtures thereof,
X is at least one element selected from P, Si, As, Ti, Zr, B, Co, Cu or Sn,
Y and Z are independently selected from W, Mo, or V,
p = is the valence of X, usually within 2 to 5,
m = 8 − p
0 < a ≦ 12.

The structures of the heteropolyacids of these complexes (i.e., salts) are difficult to determine owing to the complex nature and arrangement of the molecules. However, in general, heteropolyacids may best be described as complex inorganic substances of relatively high molecular weight in which two or more different cations or oxides of metals or metalloids are associated with varying, frequently indeterminate amounts of combined water as water of hydration. Typically, the phosphorus atom in phosphoheteropolyacids, the silicon atom in silicoheteropolyacids, etc., is regarded as the central atom of the molecule. This central atom is attached to 4 to 6 oxygen atoms. Outer $MoO_6$ or $WO_6$ octahedra are attached to the central atom through shared oxygen atoms. Thus, phosphomolybdic acid, phosphotungstic acid, phosphovanadic acid and the like can be formed. The heteropolyacids form a well known class of compounds and include, for example, phosphomolybdic acid, silicomolybdovanadic acid, titanomolybdotungstic acid, silicomolybdic acid, chromiomolybdic acid, stannotungstic acid, phosphotungstic acid, cobalt phosphomolybdate and the like. Most preferably, the heteropolyacids of the present invention are phosphotungstic or silicotungstic acid.

In a preferred embodiment of the present invention, M is selected from the lanthanide metals, most preferably M is cerium.

The catalyst of the present invention can be used either in unsupported form or supported on suitable conventional carriers as $SiO_2$, $Al_2O_3$, Zeolite, etc. However, supported catalysts are preferred because of their superior conversion and selectivity to hydrocarbons. Most especially preferred are high surface area supported catalysts (e.g., greater than 10 m²/gm) because they exhibit remarkable increases in hydrocarbon conversion.

The heteropolyacid salt catalyst of the present invention can be prepared by conventional procedures obvious to those skilled in the art. For example, the unsupported catalyst may be prepared by precipitation from an aqueous phosphotungstic acid (PTA) solution by the addition of an aqueous solution containing the metallic cation in the form of a nitrate or halide. The general reaction is:

$$M(NO_3)_3 + H_3PW_{12}O_{40} \rightarrow M^{+3}(PW_{12}O_{40})^{-3} + 3HNO_3$$

The precipitate is filtered out and dried in air for 2 hrs at 110° C. Preferably, the dried solid is then powdered in a mortar, formed into pellets and crushed to the appropriate size (e.g., 5–15 mesh).

The supported catalyst may be prepared by impregnating the support (e.g., $SiO_2$—$Al_2O_3$) with a solution of cation followed by a second impregnation with a solution of the anion. This procedure results in the deposition of the salt on the surface of the support. Of course, if the salt is soluble in the solution, the solution, itself, may be used to impregnate the support, followed by heating to remove the water.

Process Conditions

The process of the present invention is directed to the conversion of aliphatic oxygen containing organic compounds to hydrocarbons. In particular, the process of the present invention is directed to the conversion of short-chained aliphatic alcohols to $C_1+C_7$ hydrocarbons. More particularly, the process of the present invention is directed to the conversion of methanol to unsaturated hydrocarbons such as ethylene and propylene.

While methanol is the preferred feed vapor for the process of the present invention, it should be understood that other feeds such as dimethylether and methylal (dimethoxymethane) can also be utilized.

The process of the present invention comprises contacting a vaporous stream of an aliphatic oxygen containing organic compound, preferably methanol, at an elevated temperature for a time sufficient to produce hydrocarbons with a catalyst having the formula:

$$[M]^{m+}[X^{p+}Y_aZ_{12-a}O_{40}]^{-(8-p)}$$

M is at least one element selected from Group IIIA, including the lanthanides and actinides, or mixtures thereof,
X is at least one element selected from P, Si, As, Ti, Zr, B, Co, Cu or Sn,
Y and Z are independently selected from W, Mo, or V,
p = is the valence of X, usually within 2 to 5,
m = 8 − p
0 < a ≦ 12
for a time sufficient to convert said methanol to a mixture of hydrocarbon and recovering said hydrocarbons.

Typically, the process is carried out at a temperature between about 200°–400° C. Most preferably, the temperature is between 275°–325° C.

The process is normally carried out at atmospheric pressure. However, elevated pressures may be utilized in the practice of the invention, for example, 5 atmospheres.

The contact time for the reaction ranges from 1 second to 20 hours. Preferably, the contact time is between about 1 to 10 seconds.

Typically, the flow rate of the liquid feed into the reactor is between 1–10 ml/hr. Preferably, the flow rate is between about 1 to 5 ml/hr.

In a preferred embodiment of the process of the present invention, the catalyst is placed in the reactor and pretreated at an elevated temperature under an inert atmosphere prior to introduction of the methanol vapors. Most preferably, the pretreatment is at a temperature of about 325°–375° C. for about 2–4 hours.

In a further preferred embodiment of the process of the present invention, the catalyst is placed on a support having a large surface area usually in the range of about 10 m²/gm or higher. Most preferably, the surface area of the support is about 100 m²/gm.

In another preferred embodiment of the process of the present invention, the supported catalyst is a cerium salt of phosphotungstic acid.

The following specific examples are set forth to further illustrate and define the present invention.

The key feature of the data analysis set forth in the examples below is that selectivity for a given hydrocarbon product is based on carbon number. This is a more accurate reflection of the amount of $CH_3OH$ that is converted to a given product. Carbon balance is derived from a comparison of total moles of carbon found in the effluent, including unreacted MeOH, vs moles carbon (MeOH) in the feed. Carbon conversion compares the total moles of product carbon detected by Gas Chromatograph vs moles of feed MeOH. This number expresses % conversion to "useful" products, as it does not include any coke.

EXAMPLE I

Preparation of neat (unsupported) $CePW_{12}O_{40}$ reacted with MeOH at 300° C.

Catalyst Preparation

To a stirred solution of 20.01 g of phosphotungstic acid ($H_3PW_{12}O_{40}.24H_2O$) in 20 ml distilled water was added a solution of 7.87 g $Ce(NO_3)_3.6H_2O$ (excess) in 10 ml $H_2O$. After a few minutes, more Ce solution was added. The yellow precipitate which had formed was filtered off and dried 5 hr at 110° C., yield = 12 g.

Reaction 9.4 gms of the prepared catalyst were placed in a 5 cc reactor and preheated to 350° C. for 3 hr under helium. The reactor was cooled to 275° C. and methanol was fed at 1.03 ml/hr diluted with helium in the preheating zone to give a 26.2 mole % methanol feed. After one ml methanol was fed, the temperature was raised to 300° C. After 1.8 ml methanol was fed, a gas chromatograph (GC) injection of the effluent was made. The results are set forth below in Table I.

TABLE I

| Effluent | Mole % | Carbon With DME | Selectivities Without DME |
|---|---|---|---|
| $CH_4$ | 0.309 | 1.51 | 9.87 |
| Ethylene | 0.307 | 2.99 | 19.5 |
| Ethane | 0.006 | .06 | 0.39 |
| Propylene | 0.260 | 3.79 | 24.8 |
| Propane | 0.073 | 1.06 | 6.93 |
| Unsat. $C_4$ | 0.103 | 2.00 | 13.1 |

TABLE I-continued

| Effluent | Mole % | Carbon With DME | Selectivities Without DME |
|---|---|---|---|
| Sat. $C_4$ | 0.128 | 2.49 | 16.3 |
| 1-pentene | 0.027 | 0.66 | 4.31 |
| Pentane | 0.031 | 0.7 | 4.58 |
| Dimethylether | 8.761 | 84.7 | — |
| Methanol | 2.718 | — | — |
| $H_2O$ | 7.019 | — | — |

CONVERSION = 90%
Olefins are 9.4% of products, 61.7% of hydrocarbons ($C_1$–$C_5$)

EXAMPLE II

Catalyst Preparation

The catalyst was prepared by precipitation of 20.01 g of $H_3PW_{12}O_{40}$ in 20 ml $H_2O$ with a solution of 2.611 g $La(NO_3)_3.6H_2O$ in 10 ml $H_2O$. The product was filtered off and dried 2 hr at 110° C., yield = 8 g.

The reaction with methanol was carried out as in Example I using 7.04 g of $LaPW_{12}O_{40}$ in the 5 cc reactor. Runs were done at 273° C. and 298° C., then the reactor temperature was raised to 323° C. A GC injection was made of effluent gas. The results are set forth below in Table II.

TABLE II

| Effluent | Mole % | Carbon With DME | Selectivities Without DME |
|---|---|---|---|
| $CH_4$ | 0.914 | 4.43 | 19.3 |
| Ethylene | 0.402 | 3.90 | 17.0 |
| Ethane | 0.022 | 0.21 | 0.92 |
| Propylene | 0.446 | 6.48 | 28.3 |
| Propane | 0.158 | 2.30 | 10.0 |
| Unsat. $C_4$ | 0.117 | 2.27 | 9.91 |
| Sat. $C_4$ | 0.107 | 2.07 | 9.04 |
| Pentene | 0.020 | 0.48 | 2.10 |
| Pentane | 0.031 | 0.74 | 3.23 |
| Dimethylether | 7.963 | 77.1 | — |
| Methanol | 2.703 | — | — |
| $H_2O$ | 14.15 | — | — |

CONVERSION = 83.7%
Olefins are 13% of products, 55% of hydrocarbons

Tables III to V set forth below compare the results of methanol conversion using the catalyst of the present invention (Tables III & IV) with phosphotungstic acid (Table V). In each case, the catalysts used were unsupported but pretreated by air drying at 110° C. for 1 to 2 hours before pelleting and charging the reactor. The catalysts were prepared and used in the conversion of methanol in accordance with the procedures set forth in Examples I and II.

TABLE III

MeOH CONVERSION

| $M^{3+}$ | Color | % Olefins/ Hydrocarbons | % Hydrocarbon Products | % Olefins/ All Products (Including DME) |
|---|---|---|---|---|
| Ce | Light Yellow | 64 | 14.7 | 9.4 |
| Nd | Tan | 56 | 21.2 | 11.9 |
| La | Pale Yellow | 57 | 22.9 | 13.1 |
| Sm | Light Yellow | 54 | 24.0 | 13.0 |
| Dy | Yellow | 53 | 13.7 | 7.3 |
| Ho | Light Orange | 50 | 10.8 | 5.4 |
| Yb | Yellow | 41 | 15.4 | 6.3 |
| Er | Pink | 40 | 11.2 | 4.5 |
| Eu | Yellow | 35 | 39.1 | 13.7 |

T = 300° C., La at 325° C.
CT = 4 sec
LHSV = .2 hr$^{-1}$
$M^{+3}PW_{12}O_{40}^{-3}$ neat pellets 10 mesh

TABLE IV

PRODUCT CARBON SELECTIVITIES (EXCLUDING DME) IN MeOH CONVERSION OVER LANTHANIDE SALTS OF PHOSPHOTUNGSTIC ACID

| Product | Catalyst | | | | | | | | |
|---|---|---|---|---|---|---|---|---|---|
| | Ce | Nd | La | sm | Dy | Ho | Yb | Er | Eu |
| $C_1$ | 10.3 | 10.1 | 19.4 | 11.7 | 12.8 | 13.2 | 20.3 | 23.0 | 13.9 |
| $C_2=$ | 20.3 | 16.6 | 17.0 | 18.0 | 18.0 | 16.7 | 13.6 | 13.4 | 13.8 |
| $C_2$ | .4 | .7 | .9 | .9 | .8 | .6 | .9 | — | 1.6 |
| $C_3=$ | 25.8 | 24.9 | 28.3 | 20.1 | 20.7 | 20.3 | 14.7 | 14.6 | 12.2 |
| $C_3$ | 7.2 | 13.0 | 10.0 | 9.7 | 11.5 | 12.6 | 13.8 | 14.6 | 23.1 |
| $C_4=$ | 13.6 | 10.0 | 9.9 | 10.5 | 10.2 | 9.4 | 7.6 | 7.6 | 4.7 |
| $C_4$ | 17.0 | 15.4 | 9.0 | 18.4 | 15.8 | 14.8 | 18.5 | 16.3 | 22.6 |
| $C_5=$ | 4.5 | 4.0 | 2.1 | 5.5 | 4.2 | 3.9 | 5.1 | 4.6 | 4.3 |
| $C_5$ | .7 | 5.0 | 3.2 | 5.2 | 5.7 | 5.4 | 5.3 | 5.4 | 3.7 |
| $C_6=$ | — | — | — | — | — | — | — | — | — |
| $C_6$ | — | — | — | — | — | 3.7 | — | — | — |

T = 300° C., La at 325° C.
CT = 4 sec
LHSV = .2 hr$^{-1}$
CATALYST = $M^{3+}PW_{12}O_{40}^{3-}$ neat pellets, 10 mesh

TABLE V

MeOH CONVERSION OVER $H_3PW_{12}O_{40}$, NEAT CATALYST (EXCLUDING DME)

| Products | |
|---|---|
| $C_1$ | 11.6 |
| $C_2=$ | 18.1 |
| $C_2$ | 1.1 |
| $C_3=$ | 21.9 |
| $C_3$ | 10.3 |
| $C_4=$ | 11.0 |
| $C_4$ | 16.1 |
| $C_5=$ | 4.3 |
| $C_5$ | 4.6 |
| $C_6=$ | .2 |
| $C_6$ | .8 |
| DME | 65.6 |
| % uns/HC | 55.4 |
| C-conv. | 77 |
| C-bal. | 88 |

T = 300° C.
LHSV = 0.2 hr$^{-1}$
C.T. = 4 sec.
$H_3PW_{12}O_{40}$ 10 mesh pellets Table III shows that Ce, Nd, La, Sm, Dy and Ho have a 50% or better yield of olefins with respect to total hydrocarbon product. Tables IV and V show the individual carbon selectivity of the catalyst of the present invention (Table IV) compared to phosphostungstic acid (Table V). The results indicate that NdPTA, LaPTA, CePTA have higher % olefins than $H_3PTA$. CePTA has a significantly higher % olefin yield.

Table VI set forth below compares the supported catalyst of the present invention with a supported PTA catalyst. Again the conditions for preparation and using of the catalyst are the same as those set forth in Examples I and II.

TABLE VI

SUPPORTED LANTHANIDE AND ACTINIDE SALTS VS. SUPPORTED PTA

| C-Selectivity | CePTA/Alumina | | CePTA/Alumina | | $H_3$PTA/(Alumina) | | $H_4$SiTA/Alumina | | LaPTA/Alumina | | ThPTA/Alumina | |
|---|---|---|---|---|---|---|---|---|---|---|---|---|
| CO | .06 | (.15) | .07 | (.09) | .06 | (.16) | .06 | (.07) | .08 | (.1) | — | — |
| $CO_2$ | .06 | (4.7) | — | — | — | — | — | — | .02 | (.03) | .06 | (.06) |
| $CH_4$ | 2.0 | (.15) | 11.2 | (14) | 11.4 | (30.2) | 17.1 | (20.6) | 8.4 | (10.6) | 9.9 | (10.5) |
| $C_2=$ | 8.1 | (19.2) | 14.4 | (18) | 6.5 | (17.2) | 14.8 | (17.9) | 12.8 | (16.1) | 17.7 | (18.8) |
| $C_2$ | .2 | (.4) | .8 | (1) | .6 | (1.6) | 1.1 | (1.3) | .5 | (.6) | .95 | (1.0) |
| $C_3=$ | 10.65 | (25.3) | 20.9 | (26.1) | 10.5 | (27.8) | 21.6 | (26.1) | 20.6 | (25.9) | 24.4 | (26) |
| $C_3$ | 1.0 | (2.3) | 2.1 | (2.6) | .94 | (2.5) | 2.0 | (2.4) | 2.7 | (3.4) | 2.2 | (2.3) |
| $C_4=$ | 5.2 | (12.2) | 6.9 | (8.6) | 3.4 | (9.0) | 7.4 | (8.9) | 7.1 | (8.9) | 9.4 | (10.0) |
| $C_4$ | 8.4 | (20) | 13.4 | (16.8) | 2.6 | (6.9) | 11.8 | (14.2) | 11.0 | (13.9) | 16.3 | (17.4) |
| $C_5=$ | 3.1 | (7.4) | 4.6 | (5.8) | .8 | (2.1) | 4.0 | (4.8) | 3.9 | (4.9) | 5.8 | (6.2) |
| $C_5$ | 2.0 | (4.8) | 3.1 | (3.9) | 1.2 | (3.2) | 2.8 | (3.4) | 3.1 | (3.9) | 3.7 | (3.9) |
| $C_6=$ | 1.1 | (2.7) | 1.7 | (2.1) | — | — | — | — | — | — | 2.1 | (2.2) |
| $C_6$ | .3 | (.6) | 1.0 | (1.3) | — | — | — | — | .50 | (.6) | 1.4 | (1.5) |
| DME | 57.9 | | 20.0 | | 62.2 | | 17.1 | | 20.6 | | 6.1 | |
| C-balance | 106%* | | 81.5% | | 78.1% | | 55.6% | | 75.8% | | 56.2% | |
| C-conversion | 81.9% | | 72.7% | | 68.3% | | 50.3% | | 71.0% | | 54.0% | |
| % olefins of hydrocarbons (not DME) | 66.8% | | 60.5% | | 55.9% | | 57.8% | | 62.7% | | 63.4% | |
| Temp (C.) | 300 | | 325 | | 325 | | 325 | | 325 | | 327 | |
| Time on Stream | ~1.5 hr | | ~1.5 hr | | ~1.6 hr | | 3 hr | | 1.8 hr | | 2.6 hr | |

PTA = $PW_{12}O_{40}^{3-}$
SiTA = $SiW_{12}O_{40}^{4-}$
*Consequence of experimental error in GC analysis.
Parenthesis indicate selectivities without DME. DME can be recycled as a feed.

Table VI clearly demonstrates that the supported catalyst of the present invention exhibits improved olefin conversion compared with supported PTA.

Table VII set forth below demonstrates the effect that the surface area of the support for the catalyst has on the results obtained in conversion of methanol to hydrocarbons. Table VII shows that by using a 100 m²/g alumina support, a 5 fold increase in % hydrocarbons was obtained.

TABLE VIII

MeOH CONVERSION OVER SUPPORTED Ce/PTA

| Products | Catalyst | | |
|---|---|---|---|
| | Neat CePTA Pellets | CePTA/ SA3232 | CePTA/ HSAA |
| $CH_4$ | 1.51 | 1.65 | 1.84 |
| $C_2=$ | 2.99 | 5.34 | 13.21 → Increases |
| $C_2$ | .06 | .08 | .23 |
| $C_3=$ | 3.79 | 6.97 | 13.5 |
| $C_3$ | 1.06 | 1.16 | 2.73 |
| $C_4=$ | 2.0 | 3.07 | 3.19 |
| $C_4$ | 2.49 | 5.19 | 21.13 |
| $C_5=$ | .66 | 1.65 | 8.25 |
| $C_5$ | .10 | 1.11 | 1.01 |
| $C_6=$ | — | — | 3.72 |

TABLE VIII-continued
MeOH CONVERSION OVER SUPPORTED Ce/PTA

| | Catalyst | | |
|---|---|---|---|
| Products | Neat CePTA Pellets | CePTA/ SA3232 | CePTA/ HSAA |
| C$_6$ | — | — | 1.39 |
| DME | 85.3 | 73.7 | 29.8 | → Decreases
| Conv. | 72 | 82 | 80 |
| % Hydrocarbons | 14.7 | 26.3 | 70.2 | → Increases
| % Olefins/ Hydrocarbons | 64.4 | 64.9 | 59.7 |

SA3232 = Al$_2$O$_3$—SiO$_2$   30 m$^2$/g
HSAA = Alumina   100 m$^2$g
T = 300° C.

The foregoing examples clearly demonstrate the superiority of the catalyst and process of the present invention in converting low aliphatic alcohols to hydrocarbons. The catalyst of the present invention improved hydrocarbon selectivity or activity during methanol conversion. In addition, high surface area supported catalysts of the present invention dramatically increase hydrocarbon conversion compared with unsupported heteropolyacid catalysts.

The foregoing description of the preferred embodiments of the invention has been presented for purposes of illustration and description. It is not intended to be exhaustive or to limit the invention to the precise form disclosed, and obviously many modifications and variations are possible in light of the above disclosure. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A heteropolyacid salt catalyst having the formula $$[M]^{m+}[X^{p+}Y_aZ_{12-a}O_{40}]^{-(8-p)}$$

wherein
M is at least one element selected from the actinides,
X is selected from P, Si, As, Ti, Zr, B, Co, Cu or Sn;
Y and Z are independently selected from W, Mo or V;
p = the valence of X;
m = 8 − p; and
0 < a ≦ 12.

2. The catalyst of claim 1 wherein said heteropolyacid salt is deposited on a support.

3. The catalyst of claim 2 wherein said support has a surface area greater than 10 m$^2$/gm.

4. The catalyst of claim 3 wherein said support has a surface area greater than 100 m$^2$/gm.